United States Patent
Leibitzki et al.

(10) Patent No.: US 9,095,427 B2
(45) Date of Patent: Aug. 4, 2015

(54) DEVICE IN THE FORM OF A TRACHEAL CANNULA OR A PROSTHESIS FOR RESTORING THE VOICE, TO BE INSERTED IN A TRACHEOSTOMA

(75) Inventors: Harry Leibitzki, Blankenburg (DE); Steffen SÜβ, Halberstadt (DE)

(73) Assignee: PRIMED HALBERSTADT MEDIZINTECHNIK GmbH, Halberstadt (DE)

(*) Notice: Subject to any disclaimer, the term of this patent is extended or adjusted under 35 U.S.C. 154(b) by 0 days.

(21) Appl. No.: 13/879,996

(22) PCT Filed: Oct. 14, 2011

(86) PCT No.: PCT/DE2011/001868
§ 371 (c)(1),
(2), (4) Date: Apr. 24, 2013

(87) PCT Pub. No.: WO2012/055390
PCT Pub. Date: May 3, 2012

(65) Prior Publication Data
US 2013/0289722 A1    Oct. 31, 2013

(30) Foreign Application Priority Data
Oct. 29, 2010  (DE) .......................... 10 2010 049 896

(51) Int. Cl.
*A61F 2/20*   (2006.01)
*A61M 16/00*  (2006.01)
*A61M 16/04*  (2006.01)

(52) U.S. Cl.
CPC ............ *A61F 2/203* (2013.01); *A61M 16/0472* (2013.01); *A61M 2205/0266* (2013.01)

(58) Field of Classification Search
CPC ..................................................... A61M 16/00
USPC .............. 623/9; 128/200.26, 207.14–207.29; 606/108
See application file for complete search history.

(56) References Cited

U.S. PATENT DOCUMENTS

| 5,300,119 A | 4/1994 | Blom |
| 5,546,937 A | 8/1996 | Stuart et al. |
| 8,332,999 B2 * | 12/2012 | Karling et al. ............... 29/243.5 |
| 2005/0145252 A1 * | 7/2005 | Loyd et al. ............... 128/207.14 |
| 2008/0142005 A1 | 6/2008 | Schnell |
| 2008/0149107 A1 * | 6/2008 | Byatt ....................... 128/207.14 |
| 2009/0036983 A1 * | 2/2009 | Tran ................................... 623/9 |

FOREIGN PATENT DOCUMENTS

| DE | 693 17 445 | 7/1998 |
| DE | 694 32 755 | 3/2004 |

(Continued)

*Primary Examiner* — Yashita Sharma
(74) *Attorney, Agent, or Firm* — Jordan and Hamburg LLP

(57) ABSTRACT

A device for insertion in a tracheostoma which includes a cylindrical body having a longitudinal axis, a flexible flange which is provided on an outer surface of the device body and has unfolded configuration which it extends essentially from the outer surface of the body to the outside and has a folded configuration in which it is folded in the direction towards the longitudinal axis of the device body, as well as a pin-shaped insertion aid having a means for retaining the flange in its folded orientation, wherein the flange is formed by at least two wings each of which have a recess proximate a tip of the wing, in which the retaining means is removably introduced, and the wings have a shape memory that orients the wings, when unrestrained, away from the longitudinal axis of the device body.

6 Claims, 1 Drawing Sheet

(56) References Cited

FOREIGN PATENT DOCUMENTS

| DE | 10 2005 021 470 | 11/2006 |
| DE | 20 2010 002 803 | 7/2010 |
| EP | 0 551 198 | 7/1993 |
| EP | 1 099 451 | 5/2001 |
| WO | WO-87/06817 | 11/1987 |
| WO | WO-95/29649 | 11/1995 |

* cited by examiner

DEVICE IN THE FORM OF A TRACHEAL CANNULA OR A PROSTHESIS FOR RESTORING THE VOICE, TO BE INSERTED IN A TRACHEOSTOMA

BACKGROUND OF THE INVENTION

This invention relates to a device in the form of a tracheal cannula or prosthesis for restoring the voice, to be inserted into a tracheostoma, Tracheostoma prostheses (also known as tracheal cannulas or tracheostoma tubes) for treating patients without larynx (laryngectomees) with opened throat (so called tracheostoma) have been known for decades.

Apart from mere tracheal cannulas, for example for ventilating a patient via an opening below the larynx, a prosthesis can be used according to s the prior art to generate a new voice at patients with removed larynx, and said voice prosthesis (tracheostoma tube with speaking valve) creates a more or less permanent passage into the oesophagus while air, following its natural flow path, moves from the lung through a tracheostoma to the outside, Thus, the so called esophageal speaking is produced.

The tracheostoma tubes with a speaking valve mostly consist of a treacheal cannula with cannula shield and a valve receiving part for holding an external speaking valve, whereas an internal speaking valve of the tracheal cannula is accommodated in a tube between the oesophagus and the trachea so that air can escape through the internal speaking valve towards the mouth area if the tracheostoma is blocked (in case of a closed external speaking valve) and vibrations are generated for the purpose of speaking in the upper area of the oesophagus. In these arrangements, the tracheostoma is blocked manually by closing the external speaking valve at the outer surface of the tracheal cannula.

These tracheostoma cannulas mostly comprise flexible retaining collars. If properly applied, the retaining collar fits closely to the oesophagus facing surface of the party wall between the trachea and the oesophagus to avoid or at least reduce the likelihood of a dislocation of the prosthesis in the tracheostoma, Thus, said retaining collar considerably improves the support of the prosthesis (for example provides protection against the ejection of the prosthesis) but this arrangement has the disadvantage that a big retaining collar makes the insertion of a prosthesis more difficult because the tissue surrounding the tracheostoma is traumatized.

From EP 1 099 451 A3 the use of conical tips is principally known in tracheostomy.

DE 10 2005 021 470 A1 discloses an insertion aid for the percutaneous tracheostomy that comprises a shaft with a conical tip being threadable through the tracheal cannula, and said tip has a small basic diameter in a is first state and a large basic diameter in a second state, and the insertion aid has a section adjacent to the conical tip with a maximum diameter corresponding to the inner diameter of a tracheal cannula to be introduced by means of the insertion aid.

DE 694 32 755 T2 discloses a plastic insertion aid that is designed for use in tracheostomy and is provided with flexible bend sections between single noses to improve its operability.

WO87/06817 describes a prosthesis for use in sinus drainage that is provided with flexible wings that can be folded to move the prosthesis along a body channel.

DE 20 2010 002 803 U1 discloses a device for the introduction of a tracheal cannula into a tracheostoma by using an insertion aid (inserter) the tip of which being firmly bonded to a paraglider which lays on the cannula tube edge with a cover width when the insertion aid is moved into the trachal cannula tube.

DE 693 17 445 T2 discloses a device for the insertion of a prosthesis in a hole between the trachea and the esophagus (tracheostoma) to restore the voice, and said device comprises a cylindrical body having a longitudinal axis, a flexible flange which is provided on an outer surface of the device body and has a direction of use in which it extends essentially from the outer surface of the device body to the outside and has a direction of use in which it is folded flexibly towards the longitudinal axis of the device body, as well as an insertion aid having a means (e.g., gelatin capsule) for retaining the flange in its flexibly folded orientation, and said retaining means is made of a material (e.g, gelatin) that is dissoluble in the liquid existing between the esophagus and the trachea.

This device has the disadvantage that the substances being dissoluble in liquids (e.g, gelatin capsules) provoke irritations or immune reactions in the patient because they are exogenous substances or the capsules (e.g. gelatin capsules) do not dissolve completely so that the patient needs very much force to achieve an air stream through the prosthesis for the esophageal speaking.

SUMMARY OF THE INVENTION

The aim of the invention is to provide a device for insertion into a hole between the trachea and the esophagus which eliminates the drawbacks of the prior art, which, in particular, allows a correct positioning of the device in the patient in the direction of use and under an optimal air stream, without provoking irritations or immune reactions from behalf of the patient and without the risk of being ejected by the patient.

Said aim 1s achieved by a device for insertion in a tracheostoma according to the first claim. Advantageous embodiments of this invention are specified in the sub-claims.

The nature of the invention is based on the provision of a novel device for insertion in a tracheostoma which can be optimally introduced in a tracheostoma by means of flexible wings retained in their folded state by an insertion aid at the proximal end of the device and then said novel device is positioned there by unfolding the wings.

This inventive device for insertion in a tracheostoma has the advantage that a correct positioning of said device in the patient in the direction of use and under an optimal air stream is allowed without provoking irritations or immune reactions from behalf of the patient and without the risk of being ejected by the patient.

The invention is explained in detail by means of the following embodiment and the figure.

DETAILED DESCRIPTION OF THE INVENTION

Figure 1:
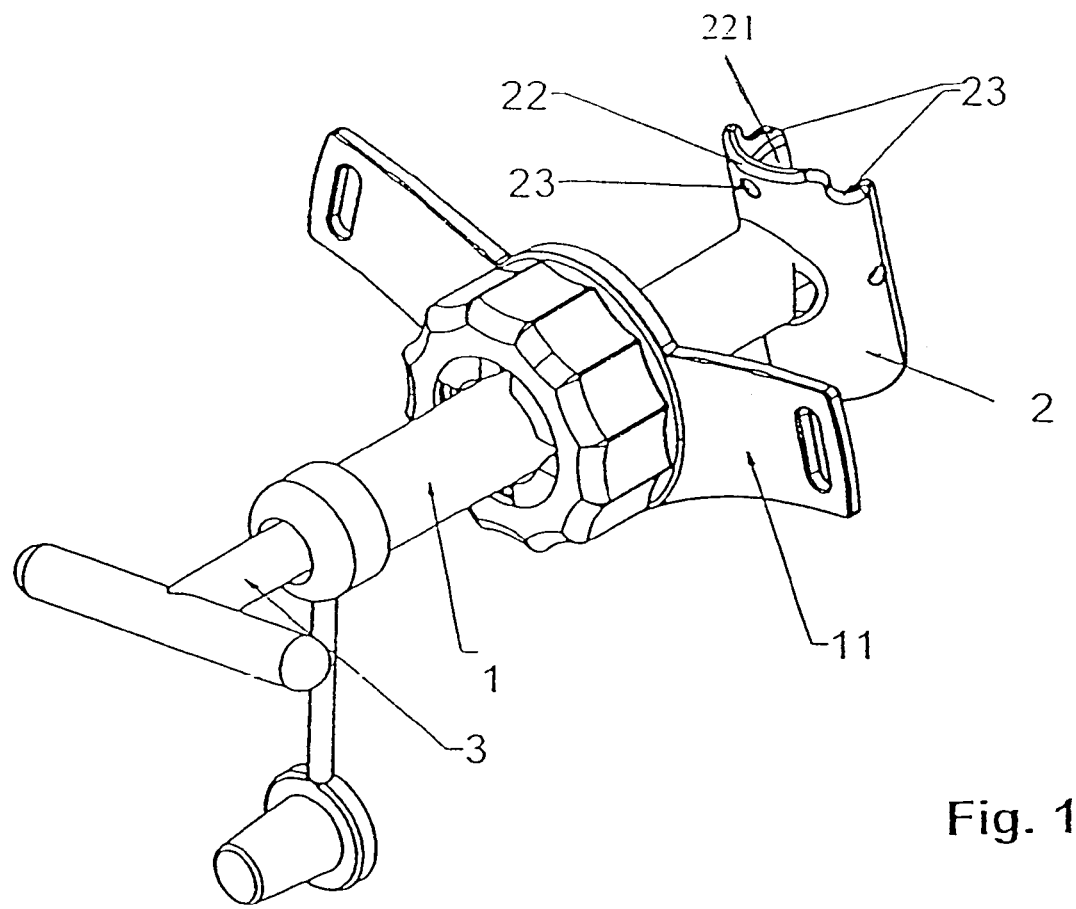
FIG. 1 is a schematic perspective view of an embodiment of an inventive device.
Figure 2:
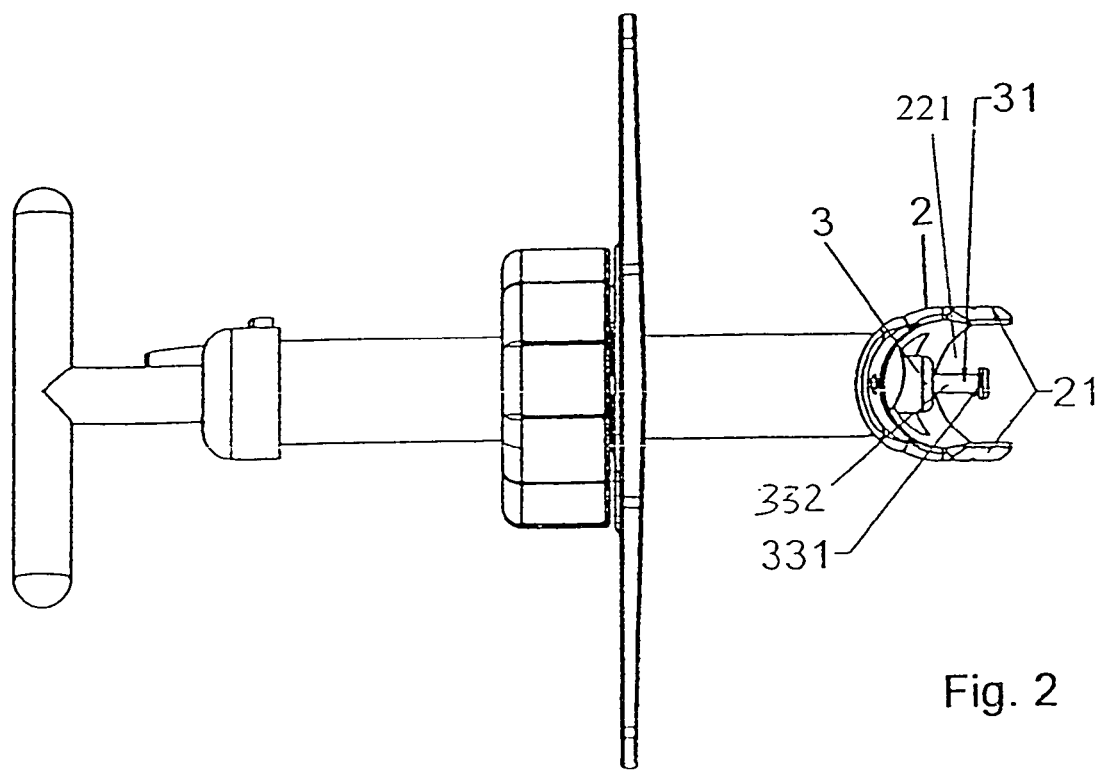
FIG. 2 is a corresponding top plan view of that embodiment.

FIGS. 1 and 2 show a device for insertion in a tracheostoma which comprises a cylindrical body (1) having a longitudinal axis. a flexible flange (2) which is provided on an outer surface of the device body (1) and has an unfolded configuration in which it extends essentially from the outer surface of the device body to the outside and can be folded, due to its flexibility, towards the longitudinal axis of the device body into a folded configuration in which it is retained by a pin-shaped insertion aid (3) having a means (31) for retaining the flange (2) in its folded configuration, the means (31) defining a flange retention member forming a portion of the pin-shaped insertion aid. as shown in FIG. 2.

According to the invention, the flange (2) is formed by at least two wings (21) provided with a recess (2) in the region of the wing tip (22) in which the means (31) of the insertion aid (3) is removably introduced. Air circulation spaces (221) are provided between the wings (21) of the flange (2).

The wings (21) folded such have a shape memory that orients the wings (21) away from the longitudinal axis of the device body (1).

The recesses (23) of the wings (21) are rounded, i.e., curved, the means (31) of the insertion aid (3) is provided with a bulbous tip (331) forming the proximal end of the insertion aid (3) via a connection (332) having a small diameter, and the maximum diameter of the tip (331) corresponds to the internal diameter of the device body (1).

The recesses (23) are open at the edge of the flange contiguous therewith so that the insertion and removal of the means (31) are facilitated.

The device body (1) is made of flexible silicone and the wings (21) are flexible enough to he folded.

On its distal side, the device body (1) is equipped with a stopper (11) in form of a shield that can be shifted and locked in place along the longitudinal axis towards the proximal orientation with said locking being achieved by a female screw provided at the stopper (screw shield). If said female screw is turned, the internal diameter of the stopper on the device body (1) will be reduced.

In this way the insertion depth towards the insertion direction can be individually adjusted.

When operating the device the pin-shaped insertion aid (3) is inserted in the cylindrical device body (1) and the wings (21) of the flange (2) are folded towards the longitudinal axis of the device body (1), and the recesses (23) in the area of the wing tips (22) are led into engagement with the distal side of the bulbous tip (331) of the means (31) for retaining the flange (2) whereby the flange (2) is retained in the folded configuration.

To unfold the wings (21) of the device body (1) towards the direction of use the insertion aid (3) is pulled out of the device body (1) so that the wings (21) of the flange (2) are unfolded.

The inventive device can be inserted in a tracheostoma of a patient.

All features disclosed in the description, the embodiments and the subsequent claims can he important for the invention both individually and in any combination.

The invention claimed is:

1. A device for insertion in a tracheostoma, the device comprising a cylindrical body having a longitudinal axis, a flexible flange which is provided on an outer surface of the device body and has an unfolded configuration in which it extends outwardly, substantially away from the outer surface of the device and has a folded configuration in which it is folded towards the longitudinal axis of the device body, as well as an insertion aid having a flange retention member for retaining the flange in its folded configuration, wherein the flange is formed by at least two wings each of which has a recess proximate a tip of the wing and which the flange retention member is adapted to disengageably engage, and the wings have a shape memory that orients the wings, when not retained, away from the longitudinal axis of the device body, the recesses being rounded and the flange retention member being provided with a bulbous tip forming a proximal end of the insertion aid via a connection having a diameter smaller than that of the bulbous tip, and maximum external diameters of the insertion aid and of the bulbous tip correspond to an internal diameter of the device body.

2. The device for insertion in a tracheostoma according to claim 1, wherein the device body is made of flexible silicone.

3. The device for insertion in a tracheostoma according to claim 2, wherein the wings have a shape memory and are flexibly foldable.

4. The device for insertion in a tracheostoma according to claim 1, wherein each of the recesses is open at a wing edge contiguous therewith.

5. The device for insertion in a tracheostoma according to claim 1, wherein a distal side of the device body is provided with a stopper in form of a shield, said stopper being movable and lockable in place on the device body along the longitudinal axis.

6. The device for insertion in a tracheostoma according to claim 1, wherein air circulation spaces are provided between the wings of the flange.

* * * * *